US008052602B2

(12) United States Patent
Sunagawa et al.

(10) Patent No.: US 8,052,602 B2
(45) Date of Patent: Nov. 8, 2011

(54) ULTRASONIC DIAGNOSTIC APPARATUS

(75) Inventors: Kazuhiro Sunagawa, Miyagi (JP);
Hiroshi Kanai, Miyagi (JP)

(73) Assignee: Panasonic Corporation, Osaka (JP)

( * ) Notice: Subject to any disclaimer, the term of this patent is extended or adjusted under 35 U.S.C. 154(b) by 666 days.

(21) Appl. No.: 12/095,381

(22) PCT Filed: Jun. 15, 2006

(86) PCT No.: PCT/JP2006/312057
§ 371 (c)(1),
(2), (4) Date: May 29, 2008

(87) PCT Pub. No.: WO2007/063619
PCT Pub. Date: Jun. 7, 2007

(65) Prior Publication Data
US 2009/0163805 A1    Jun. 25, 2009

(30) Foreign Application Priority Data

Nov. 30, 2005   (JP) ................................. 2005-345772

(51) Int. Cl.
*A61B 8/00*    (2006.01)
(52) U.S. Cl. ........................................ 600/437; 600/443
(58) Field of Classification Search ........... 600/437–463
See application file for complete search history.

(56) References Cited

U.S. PATENT DOCUMENTS

| 5,293,870 | A | * | 3/1994 | Ophir et al. .................... 600/437 |
| RE34,663 | E | * | 7/1994 | Seale ............................ 600/587 |
| 5,524,636 | A | * | 6/1996 | Sarvazyan et al. ............. 600/587 |
| 5,810,731 | A | * | 9/1998 | Sarvazyan et al. ............ 600/438 |
| 7,731,661 | B2 | * | 6/2010 | Salcudean et al. ............. 600/437 |
| 2003/0135124 | A1 | * | 7/2003 | Russell ......................... 600/500 |
| 2004/0034304 | A1 | * | 2/2004 | Sumi ............................. 600/439 |

(Continued)

FOREIGN PATENT DOCUMENTS

JP    62-172946    7/1987

(Continued)

OTHER PUBLICATIONS

Kazuhiro Sunagawa, Hiroshi Kanai, Yoshiro Koiwa, and Motonao Tanaka; Measurement of Vibration Propagation from Intima to Adventitia of the Arterial Wall and thier Analysis.

(Continued)

*Primary Examiner* — Sanjay Cattungal
(74) *Attorney, Agent, or Firm* — Pearne & Gordon LLP (57) ABSTRACT

An object of the invention is to provide an ultrasonic diagnostic apparatus that can conduct elastic modulus measurement with high accuracy without enlarging the circuit scale. A calculator 3 uses a signal from a receiver-transmitter 2 to calculate the motion velocity or the move displacement of body tissue and the strain variation of the body tissue. A frequency analyzer 4 conducts frequency analysis of the motion velocity and the move displacement of the body tissue found in the calculator 3. A strain induced by stress and elastic wave separator 5 separates a frequency component with strain of an arterial wall caused by blood pressure change caused by pulsation of the heart, a frequency component of vibration caused by flow of blood into the lumen of artery, and a frequency component of noise based on the determination result of the frequency analyzer 4. An elastic modulus calculator 6 calculates the elastic modulus of the body tissue based on the calculation result of the motion of the body tissue obtained in the calculator 3, etc.

10 Claims, 8 Drawing Sheets

U.S. PATENT DOCUMENTS

| | | | |
|---|---|---|---|
| 2005/0119568 A1* | 6/2005 | Salcudean et al. | 600/437 |
| 2006/0173319 A1* | 8/2006 | Sumi | 600/437 |
| 2006/0184020 A1* | 8/2006 | Sumi | 600/437 |
| 2006/0184025 A1* | 8/2006 | Sumi | 600/438 |
| 2006/0211909 A1* | 9/2006 | Anstadt et al. | 600/16 |
| 2007/0167813 A1* | 7/2007 | Lee et al. | 600/459 |
| 2007/0282202 A1* | 12/2007 | Maurice et al. | 600/438 |
| 2007/0299340 A1* | 12/2007 | Liu et al. | 600/437 |

FOREIGN PATENT DOCUMENTS

| | | |
|---|---|---|
| JP | 10-005226 | 1/1998 |
| JP | 11-151242 | 6/1999 |
| JP | 2000-201932 | 7/2000 |
| JP | 2003-275211 | 9/2003 |
| JP | 2005-074146 | 3/2005 |

OTHER PUBLICATIONS

Hans L. Oestreicher; "Field and Impedance of an Oscillating Sphere in a Viscoelastice Medium with an Application to Biophysics"; The Journal of the Acoustical Society of America; vol. 23, No. 6; Nov. 1951.

Yoshiki Yamakoshi, Junichi Sato, and Takuso Sato; Ultrasonic Imaging of Internal Vibration of Soft Tissue under Forced Vibration; IEEE Transactions on Ultrasonics, Ferroelectrics, and Frequency Control; vol. 37 No. 2; Mar. 1990.

Kazuhiro Sunagawa, Hiroshi Kanai, Yoshiro Koiwa, and Motonao Tanaka; Time-Frequency Analysis of Viration Propagation from Intima to Adventitia of Arterial Wall.

* cited by examiner

ULTRASONIC DIAGNOSTIC APPARATUS

TECHNICAL FIELD

This invention relates to an ultrasonic diagnostic apparatus for measuring the shape characteristic or the property characteristic of body tissue using ultrasonic waves.

BACKGROUND ART

A technique of discriminating and identifying body tissue using a difference in the elastic modulus caused by elastic fiber, collagen fiber, fat, a thrombus, etc., making up tissue in a biological body is known as one of means for discriminating and identifying the properties of tissue in a biological body; a technique of measuring strain occurring when stress is applied to tissue in a biological body and finding a compressive elastic modulus from the relationship between the stress and the strain as shown in patent document 1 and a technique of finding the propagation characteristic of an elastic wave propagating in body tissue and finding mechanical impedance or elastic modulus from the propagation characteristic as shown in patent document 2, non-patent document 1, non-patent document 2, and non-patent document 3 are known.

If noise is contained in the motion velocity or move displacement of any of plural interest points or interest regions, the effect of the noise also appears in the calculated elastic modulus. Thus, a technique of removing noise if the target signal contains noise and interpolating with values at the times before and after the noise occurrence time or providing an ideal signal to approximate the signal, for example, as shown in patent document 3, patent document 4, and patent document 5 is known.

Patent document 1: JP-A-10-5226
Patent document 2: JP-A-62-172946
Patent document 3: JP-A-11-151242
Patent document 4: JP-A-2000-201932
Patent document 5: JP-A-2003-275211
Non-patent document 1: H. L. Oestreicher, "Field and Impedance of an Oscillating Sphere in a Viscoelastic Medium with an Application to Biophysics," The Journal of the Acoustical Society of America, Vol. 23, No. 6, 1951.
Non-patent document 2: Y. Yamakoshi, J. Sato, T Sato, "Ultrasonic Imaging of Internal Vibration of Soft Tissue under Forced Vibration," IEEE Trans. UFFC, Vol. 37, No. 2, 1990.
Non-patent document 3: K. Sunagawa, H. Kanai, Y. Koiwa, M. Tanaka, "Time-Frequency Analysis of Vibration Propagation from Intima to Adventitia of Arterial Wall," 2002 IEEE Ultrasonics Symposium Proceedings, Vol. 2, 2002.

DISCLOSURE OF THE INVENTION

Problems to be Solved by the Invention

The technique of finding an elastic modulus or a compressive elastic modulus from strain occurring when stress is applied to tissue in a biological body requires a plurality of measurement means including strain measurement means with an ultrasonic diagnostic apparatus and stress measurement means with a sphygmomanometer as shown in patent document 1, for example, to find the compressive elastic modulus of an arterial wall; the parts that can be measured with the plurality of measurement means are limited, particularly the parts of a biological body to which a sphygmomanometer can be applied are limited to an upper arm, etc., and the measurement parts of the stress and strain need to be the same parts and thus the strain measurement parts using ultrasonic waves are limited to the parts to which a sphygmomanometer can be applied.

In the technique of finding the propagation characteristic of an elastic wave propagating in body tissue with a transfer function and finding an elastic modulus or a shear elastic modulus from the propagation characteristic as shown in patent document 2, periodical motion involving strain caused by pulsation of the heart exists in the parts of an arterial wall, a cardiac muscle wall, etc., and thus may be unable to be separated from motion caused by an elastic wave generated in body tissue using a vibrator, etc.

In the technique of providing an ideal signal for comparison to determine noise as for the target signal as shown in patent document 3 or 4, an enormous ideal signal needs to be provided and the circuit scale becomes large because the motion state of body tissue varies from one specimen to another and further the state of body tissue also changes in the same specimen from moment to moment.

To find an elastic modulus using both of the motion of body tissue relative to the stress of the body tissue and the motion caused by elastic wave propagation, it is necessary to provide an ideal signal combining the motion of body tissue relative to the stress of the body tissue with the motion caused by elastic wave propagation.

It is therefore an object of the invention to provide an ultrasonic diagnostic apparatus that can conduct elastic modulus measurement with high accuracy without enlarging the circuit scale.

Means For Solving the Problems

Generally, the nature of motion of an elastic body like body tissue depends on the elastic modulus, the viscosity, the density, the shape, etc., of the elastic body. The motion of the elastic body is occurrence of strain accompanying blood pressure change, propagation of vibration from a vibration source inside or outside the biological body (occurrence of an elastic wave), etc., for example, as an arterial wall. For example, for the arterial wall, motion involving strain caused by blood pressure change and vibration caused by flow of blood into the lumen of artery exist at the same time.

Figure 4:
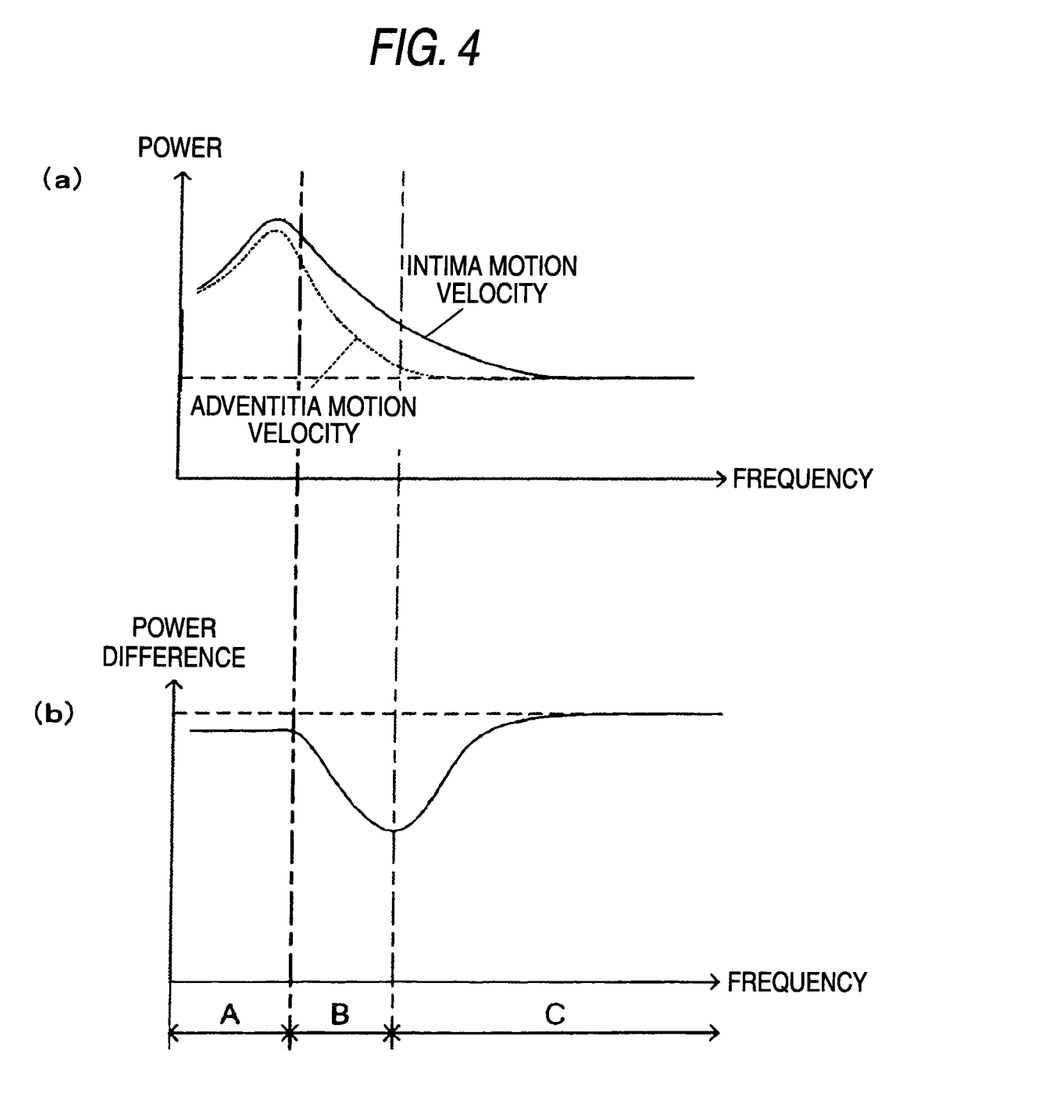
FIG. 4 is a schematic drawing to show power spectra of the motion velocities of the intima and adventitia of an arterial wall and the power difference between both power spectra.

FIG. 4(a) is a schematic drawing to show power spectra of the motion velocities of the intima and adventitia of an arterial wall, and FIG. 4(b) is a schematic drawing to show the power difference between both power spectra.

As shown in FIG. 4(a), the power spectrum of the motion velocity of the intima of the arterial wall and the power spectrum of the motion velocity of the adventitia of the arterial wall have nature that the power becomes the maximum in a frequency band of several ten Hz from direct current accompanying pulsation of the heart mainly and decreases with an increase in the frequency. The vibration caused by blood pressure change of arterial wall vibration involves strain of the arterial wall and a vibration component amplitude difference occurs between the intima and the adventitia of the arterial wall. It is known that the frequency component of the motion involving strain of the arterial wall caused by blood pressure change is a frequency band of about several ten Hz from direct current. In FIG. 4, the frequency component of the vibration of the arterial wall caused by blood pressure change is indicated as frequency band A.

The vibration caused by flow of blood into the lumen of artery has a minute amplitude as compared with the motion involving strain of the arterial wall caused by blood pressure change and is a frequency band of ten and several Hz to about hundred Hz. In FIG. 4, the frequency component of the vibration caused by flow of blood into the lumen of artery is indicated as frequency band B.

The minute vibration component occurring in the intima of the arterial wall propagates as a shear elastic wave from the intima to the adventitia of the arterial wall. It is known that attenuation α is expressed as a function of frequency f, and phase β also changes. There is a relationship among the attenuation α, the phase β, and the elastic characteristic of body tissue, and the attenuation α of the shear elastic wave in the body tissue and the phase β are found according to (expression 1) from shear elastic modulus $\mu_1$, shear viscosity $\mu_2$, body tissue density ρ, and angular frequency ω (non-patent document 1, non-patent document 2).

[Number 1]

$$\begin{cases} \alpha(\omega) = \left( \dfrac{\rho\omega^2 \left( \sqrt{\mu_1^2 + \omega^2\mu_2^2} - \mu_1 \right)}{2(\mu_1^2 + \omega^2\mu_2^2)} \right)^{\frac{1}{2}} \\ \beta(\omega) = \left( \dfrac{\rho\omega^2 \left( \sqrt{\mu_1^2 + \omega^2\mu_2^2} + \mu_1 \right)}{2(\mu_1^2 + \omega^2\mu_2^2)} \right)^{\frac{1}{2}} \end{cases} \quad \text{(Expression 1)}$$

Where the angular frequency ω is provided by converting the frequency f into the dimension of angle and is found as ω=2πf. π is the circle ratio.

The shear elastic modulus $\mu_1$ and the shear viscosity $\mu_2$ of the body tissue are found according to (expression 2) from the attenuation α of the shear elastic wave in the body tissue and the phase β (non-patent document 1, non-patent document 2).

[Number 2]

$$\begin{cases} \mu_1 = \dfrac{\rho\omega\beta^2(\alpha^2 - \beta^2)^2}{(\alpha^2 + \beta^2)^2} \\ \mu_2 = \dfrac{2\rho\omega\alpha\beta}{(\alpha^2 + \beta^2)^2} \end{cases} \quad \text{(Expression 2)}$$

Since the attenuation α of the shear elastic wave increases with an increase in the frequency, the difference between the power spectrum of the motion velocity of the intima of the arterial wall and the power spectrum of the motion velocity of the adventitia of the arterial wall increases with an increase in the frequency (see the frequency band B).

Using the fact that the attenuation α of the shear elastic wave increases with an increase in the frequency, the shear elastic modulus $\mu_1$ and the shear viscosity $\mu_2$ of the body tissue can be found approximately from the attenuation α.

That is, if both sides of the expression of the attenuation α in (expression 1) are squared, the result becomes as in (expression 3) and approximation can be made using (expression 4) in the frequency band where the square value becomes $\omega\mu_2 \gg \mu_1$.

[Number 3]

$$\alpha(\omega)^2 = \left( \dfrac{\rho\omega^2 \left( \sqrt{\mu_1^2 + \omega^2\mu_2^2} - \mu_1 \right)}{2(\mu_1^2 + \omega^2\mu_2^2)} \right) \quad \text{(Expression 3)}$$

-continued $$\hat{\alpha}(\omega)^2 = \dfrac{\rho}{2\mu_2}\omega - \dfrac{\rho\mu_1}{2\mu_2^2} \quad \text{(Expression 4)}$$

Here, assuming that the body tissue density ρ, the shear elastic modulus $\mu_1$, and the shear viscosity $\mu_2$ are constant independently of the frequency, (expression 4) can be represented by a linear function concerning ω as shown in (expression 5).

[Number 4]

$$\hat{\alpha}(\omega)^2 = A\omega + B \quad \text{(Expression 5)}$$

where $A = \dfrac{\rho}{2\mu_2}$ $B = -\dfrac{\rho\mu_1}{2\mu_2^2}$

Using inclination A and intercept B, the shear elastic modulus $\mu_1$ and the shear viscosity $\mu_2$ can be found according to (expression 6) (see non-patent document 3).

[Number 5]

$$\begin{cases} \hat{\mu}_1 = -\dfrac{2\mu_2^2 B}{\rho} \\ \hat{\mu}_2 = \dfrac{\rho}{2A} \end{cases} \quad \text{(Expression 6)}$$

Figure 7:
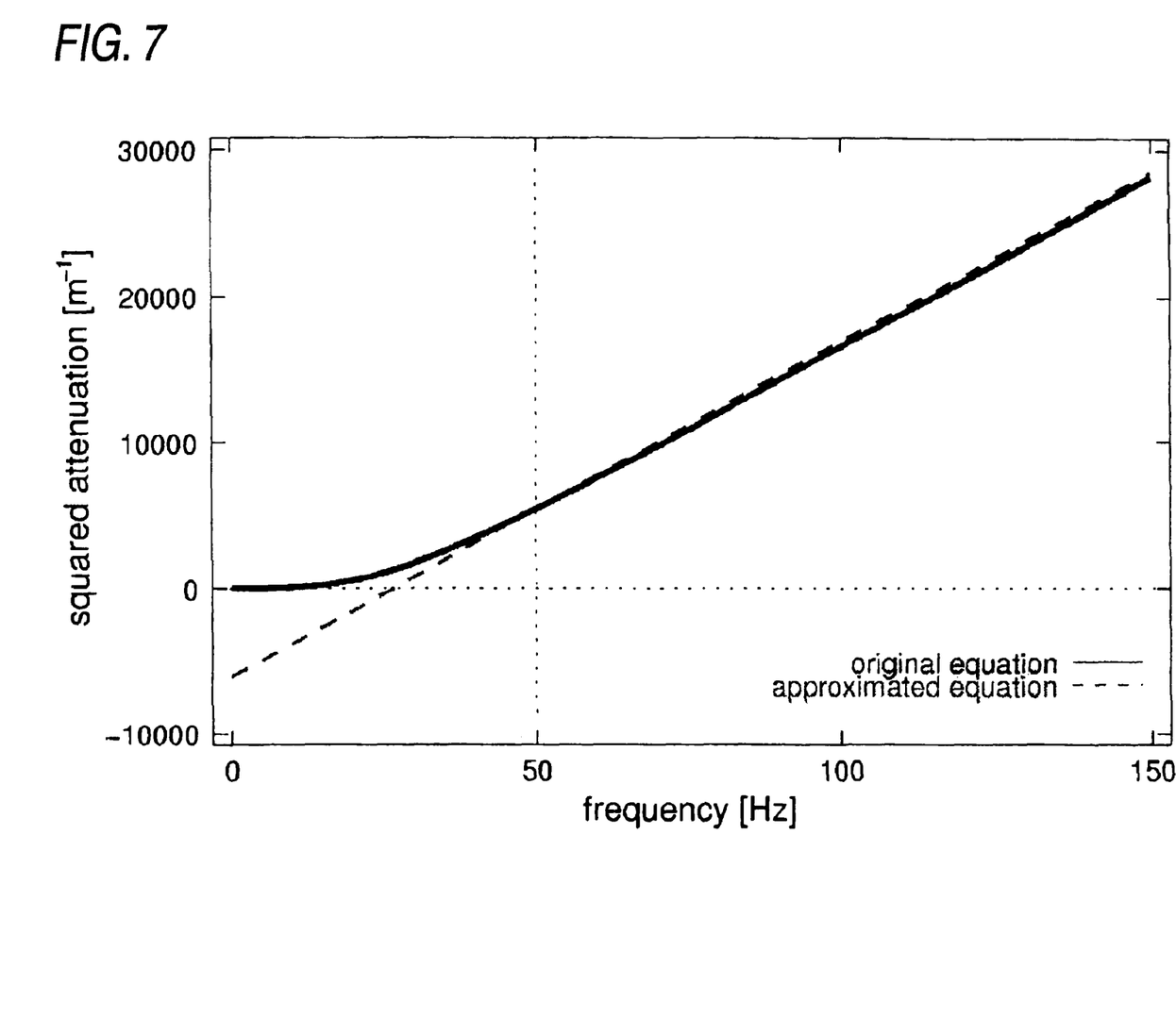
FIG. 7 is a drawing to show the frequency characteristic of the square value of the attenuation of a shear elastic wave of an example of general body tissue and the frequency characteristic approximated by a linear function.

FIG. 7 shows the frequency characteristic of the square value of the attenuation of a shear elastic wave when the density of general body tissue (ρ=1.1×10³ kg), shear elastic modulus ($\mu_1$=2.5 kPa), and shear viscosity ($\mu_2$=15 Pa·s) and the frequency characteristic approximated by a linear function.

As seen in FIG. 7, the frequency characteristic of elastic wave attenuation can be approximated by a linear function in a frequency band of about 50 Hz or more in body tissue, and the technique makes it possible to estimate the shear elastic modulus and the shear viscosity of the body tissue from the frequency characteristic of only the attenuation of the shear elastic wave.

On the other hand, in the frequency band where the square value becomes $\omega\mu_2 \ll \mu_1$, the square value of the attenuation of the shear elastic wave is represented by (expression 7) and the angular frequency ω0 of the inflection point transiting from (expression 7) to (expression 4) is represented by (expression 8).

[Number 6]

$$\hat{\alpha}(\omega)^2 \approx 0 \quad \text{(Expression 7)}$$

$$\omega_0 = \dfrac{\mu_1}{\mu_2} \quad \text{(Expression 8)}$$

The frequency spectrum of white noise of general noise is constant independently of the frequency and if the power spectrum of the motion velocity of the intima of the arterial wall and the power spectrum of the motion velocity of the adventitia of the arterial wall approach a noise level, the difference between the power spectrum of the motion velocity of the intima of the arterial wall and the power spectrum of the motion velocity of the adventitia of the arterial wall decreases with an increase in the frequency as shown in FIG. 4(b). The frequency component of mainly a noise component is indicated as frequency band C in FIG. 4(b).

As shown in FIG. 4(b), in the power spectrum difference of the motion velocities between two interest points, an inflection point exists on the boundary between the frequency bands A and B and the boundary between the frequency bands B and C and thus it is made possible to separate the frequency bands A, B, and C by finding the inflection points. The inflection point can be found by differentiating the power spectrum difference and detecting the frequency at which a peak occurs. In the peak detection, one threshold value may be preset.

The power spectrum difference of motion velocity or move displacement between two interest points has almost no inclination in the frequency band A, has a negative inclination in the frequency band B, and has a positive inclination in the frequency band C and thus the inclination of the power vector difference of motion velocity or move displacement between two interest points with respect to the frequency is found and the frequency at which the inclination changes is detected, whereby it is made possible to separate the frequency bands A, B, and C.

In the description, the motion velocity of the arterial wall is taken as an example, but the similar result of the frequency characteristic is also obtained in the move displacement of the arterial wall of the time integration of the motion velocities of the arterial wall.

An ultrasonic diagnostic apparatus of the invention is an ultrasonic diagnostic apparatus for measuring the shape characteristic or the property characteristic of body tissue and includes either of a velocity calculator which calculates a motion velocity of body tissue and a move displacement calculator which calculates a move displacement of the body tissue; a strain variation calculator which calculates the strain variation of the body tissue based on the motion velocity or the move displacement; a stress variation detector which detects a stress variation applied to the body tissue; a frequency analyzer which conducts frequency analysis on at least one of the motion velocity and the move displacement; a strain induced by stress and elastic wave separator which separates a strain induced by stress component based on motion of the body tissue caused by stress change of the body tissue motion and an elastic wave component based on an elastic wave propagation characteristic propagating in the body tissue, from at least one of the motion velocity, the move displacement, the strain variation, and the stress variation; and an elastic modulus calculator which calculates a compressive elastic modulus based on motion of the body tissue caused by stress change based on the strain variation and the stress variation and also calculating at least one of shear elastic modulus and shear viscosity based on the elastic wave propagation characteristic.

The ultrasonic diagnostic apparatus of the invention contains an ultrasonic diagnostic apparatus wherein the velocity calculator, the move displacement calculator, and the strain variation calculator have functions of finding spatial distributions of the motion velocity, the move displacement, and the strain variations on a plurality of interest points or interest regions set in the body tissue.

The ultrasonic diagnostic apparatus of the invention contains an ultrasonic diagnostic apparatus wherein the velocity calculator, the move displacement calculator, and the strain variation calculator have functions of finding spatial average values of the motion velocities, the move displacements, and the strain variations.

The ultrasonic diagnostic apparatus of the invention contains an ultrasonic diagnostic apparatus wherein the frequency analyzer has a function of calculating the frequency characteristic of a transfer function on at least one of the motion velocity and the move displacement between at least two or more interest points in the body tissue.

The ultrasonic diagnostic apparatus of the invention contains an ultrasonic diagnostic apparatus wherein the frequency analyzer has a function of calculating a power spectrum difference or the square value of the attenuation on at least one of the motion velocity and the move displacement between at least two or more interest points in the body tissue and further calculating an inclination relative to the power spectrum difference or the frequency of the square value of the attenuation.

The ultrasonic diagnostic apparatus of the invention contains an ultrasonic diagnostic apparatus wherein the strain induced by stress and elastic wave separator separates the strain induced by stress components and the elastic wave components of the motion velocity, the move displacement, the strain variation, and the stress variation based on the inclination relative to the power spectrum difference or the frequency of the square value of the attenuation and further removes a noise component.

The ultrasonic diagnostic apparatus of the invention contains an ultrasonic diagnostic apparatus wherein the strain induced by stress and elastic wave separator is implemented as a band-pass filter and/or a band limiting filter.

An ultrasonic diagnostic apparatus of the invention is an ultrasonic diagnostic apparatus for measuring the shape characteristic or the property characteristic of body tissue and includes either of a velocity calculator which calculates the motion velocity of body tissue and a move displacement calculator which calculates the move displacement of the body tissue; a frequency analyzer which conducts frequency analysis on at least one of the motion velocity and the move displacement; a strain induced by stress and elastic wave separator which separates a strain induced by stress component based on motion of the body tissue caused by stress change of the body tissue motion and an elastic wave component based on an elastic wave propagation characteristic propagating in the body tissue, from at least one of the motion velocity and the move displacement; and an elastic modulus calculator for calculating at least either of shear elastic modulus and shear viscosity based on the elastic wave propagation characteristic.

The ultrasonic diagnostic apparatus of the invention contains an ultrasonic diagnostic apparatus further including a display for displaying information based on the calculation result of the elastic modulus calculator.

ADVANTAGES OF THE INVENTION

According to the invention, there can be provided an ultrasonic diagnostic apparatus that can conduct elastic modulus measurement with high accuracy without enlarging the circuit scale. Further, according to the invention, the shear elastic modulus and the shear viscosity can be measured at the same time and more detailed discrimination and identification of the body tissue can be realized, for example, as distinguishing between fat and a thrombus with almost the same compressive elastic modulus and shear elastic modulus.

DESCRIPTION OF REFERENCE NUMERALS AND SIGNS

| | |
|---|---|
| 1 | Ultrasonic probe |
| 2 | Receiver-transmitter |
| 3 | Calculator |
| 4 | Frequency analyzer |
| 5 | Corrector |
| 6 | Elastic modulus calculator |
| 7 | Display |
| 31 | Motion velocity calculator |
| 32 | Move displacement calculator |
| 33 | Strain variation calculator |
| 61 | Compressive elastic modulus calculator |
| 62 | Shear elastic modulus calculator |
| 104 | Controller |
| 105 | Memory unit |
| 106 | Stress detector |
| 201 | Body tissue surface |
| 202 | Arterial wall |
| 301 | Ultrasonic beam |
| 401a | Move displacement waveform of intima of arterial wall |
| 401b | Move displacement waveform of adventitia of arterial wall |
| 402 | Strain change waveform of arterial wall |

BEST MODE FOR CARRYING OUT THE INVENTION

An embodiment of the invention will be discussed with the accompanying drawings.

Figure 1:
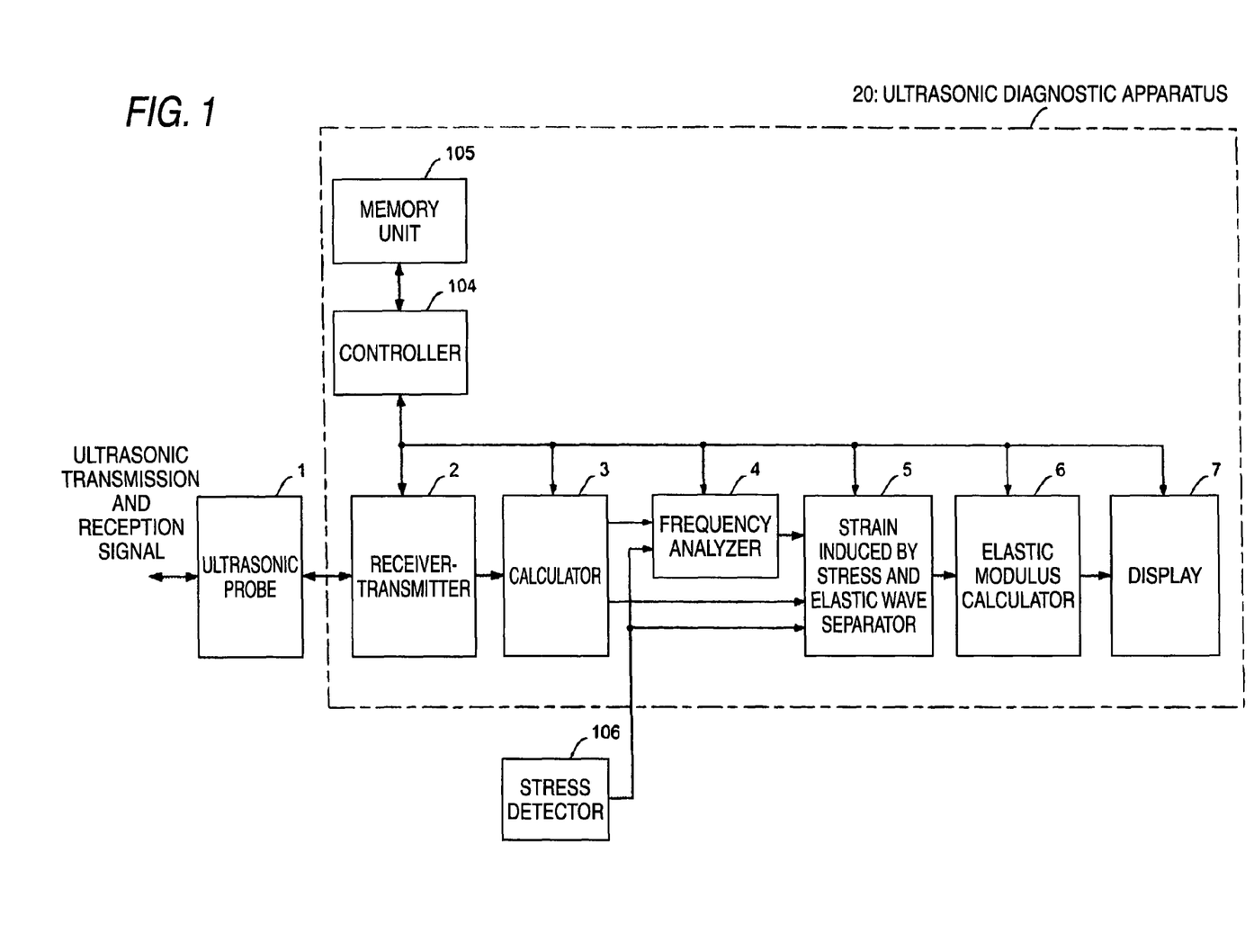
FIG. 1 is a block diagram of an ultrasonic diagnostic apparatus of an embodiment of the invention.

FIG. 1 is a block diagram of an ultrasonic diagnostic apparatus of an embodiment of the invention. An ultrasonic diagnostic apparatus 20 in FIG. 1 measures the shape characteristic or the property characteristic of a biological body using an ultrasonic probe 1 and particularly is used suitably to measure the elastic modulus of body tissue. Here, the shape characteristic of a biological body refers to the motion velocity of body tissue based on the shape of the body tissue or time change of the shape, move displacement of the integral value of the motion velocities, the strain variation between two points set in the body tissue, etc. The property characteristic of a biological body refers to the elastic modulus of body tissue, etc. The ultrasonic diagnostic apparatus 20 includes a receiver-transmitter 2, a calculator 3, a frequency analyzer 4, a strain induced by stress and elastic wave separator 5, an elastic modulus calculator 6, a display 7, a controller 104, and a memory unit 105.

The ultrasonic probe 1 is used to transmit an ultrasonic wave to body tissue to be measured and receive an ultrasonic echo provided by reflecting the transmitted ultrasonic wave on the body tissue. The receiver-transmitter 2 generates a predetermined drive pulse signal for driving the ultrasonic probe 1 and outputs the drive pulse signal to the ultrasonic probe 1 and also delays and combines the ultrasonic echo received at the ultrasonic probe 1.

The calculator 3 uses the delayed and combined signal in the receiver-transmitter 2 to calculate the motion velocity of body tissue or the move displacement and the strain variation. The frequency analyzer 4 conducts frequency analysis of the motion velocity of the body tissue and the move displacement found in the calculator 3.

The strain induced by stress and elastic wave separator 5 separates the frequency component with strain of an arterial wall caused by blood pressure change caused by pulsation of the heart, the frequency component of vibration caused by flow of blood into the lumen of artery, and the frequency component of noise based on the determination result of the frequency analyzer 4. The elastic modulus calculator 6 calculates the elastic modulus of the body tissue based on the calculation result of the motion of the body tissue obtained in the calculator 3, etc. The display 7 displays the elastic characteristic of the body tissue calculated in the elastic modulus calculator 6.

The controller 104 controls the receiver-transmitter 2, the calculator 3, the frequency analyzer 4, the strain induced by stress and elastic wave separator 5, the elastic modulus calculator 6, and the display 7. Various pieces of information for the controller 104 to perform control are stored in the memory unit 105.

A stress detector 106 detects stress applied to the point of interest or the region of interest in the body tissue. To measure the stress applied to an arterial wall as in a measurement example shown in FIG. 3, a sphygmomanometer is preferred. To apply stress from the surface of body tissue, a pressure sensor may be installed on the surface of the body tissue.

Figure 3:
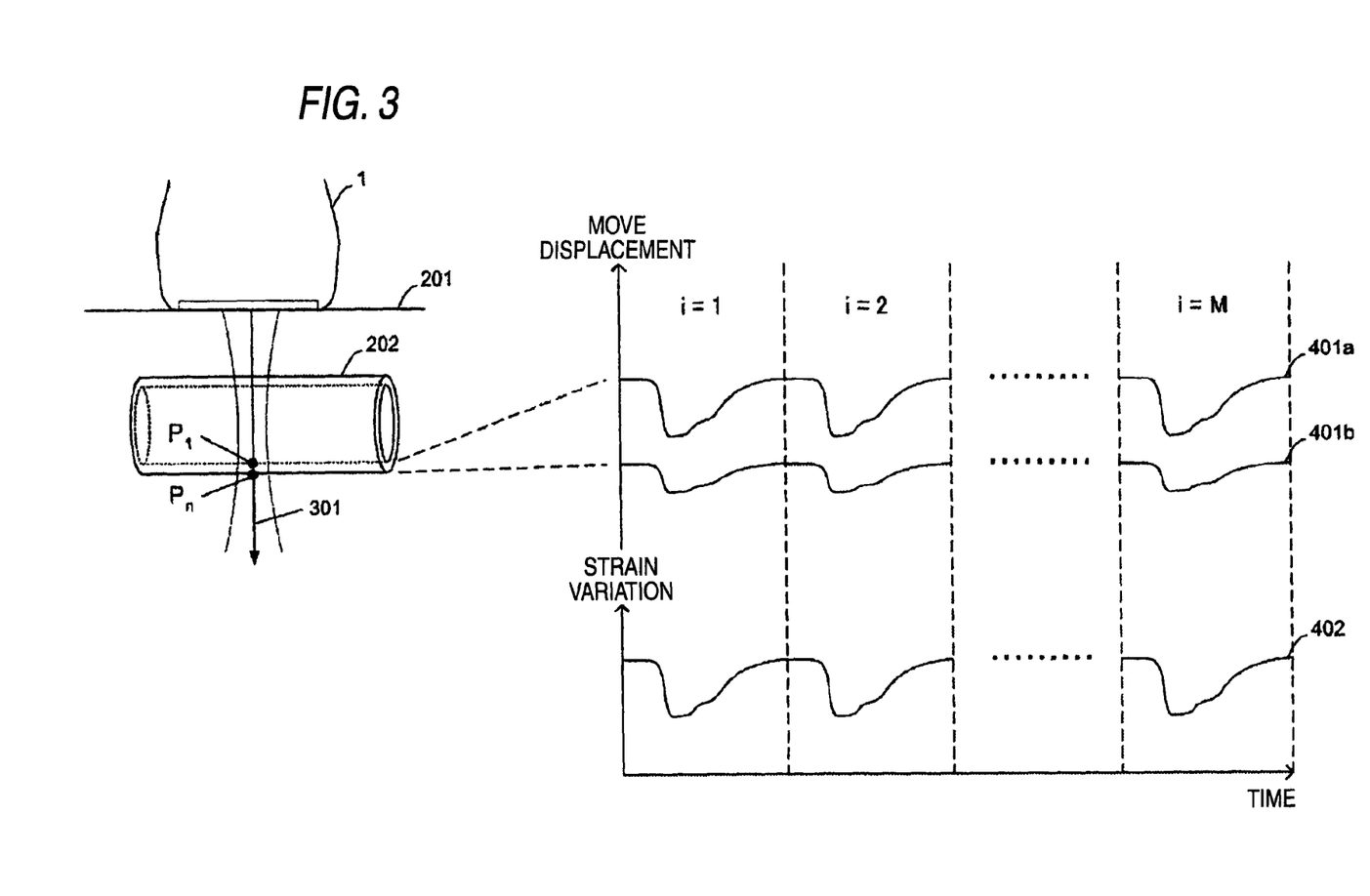
FIG. 3 is a schematic drawing to show how an ultrasonic wave is transmitted and received with an ultrasonic probe, move displacement of an arterial wall is measured, and strain change is calculated.

To use the ultrasonic diagnostic apparatus 20 to measure the shape characteristic or the property characteristic of an arterial wall of an example of body tissue, an ultrasonic wave is transmitted and received with the ultrasonic probe 1, the move displacement of the arterial wall is measured, and strain change is calculated as shown in FIG. 3. FIG. 3 is a schematic drawing to show how interest points are set in the intima and the adventitia of the arterial wall and move displacement and strain accompanying the cardiac beat are measured, move displacement of the intima and the adventitia of the arterial wall, and strain amount change of the arterial wall.

Specifically, an ultrasonic wave is transmitted from the ultrasonic probe 1 installed on a body tissue surface 201 to an arterial wall 202 in the body tissue, and an ultrasonic echo produced on the arterial wall 202 is received at the ultrasonic probe 1. The transmitted ultrasonic wave and the received ultrasonic wave form an ultrasonic beam 301. If the interest points are set in the intima and the adventitia of the arterial wall positioned on the ultrasonic beam 301, the calculator 3 can find the difference between a move displacement waveform 401a of the intima and a move displacement waveform 401*b* of the adventitia and can find a strain variation 402 of the arterial wall accompanying blood pressure change caused by the cardiac beat.

Figure 2:
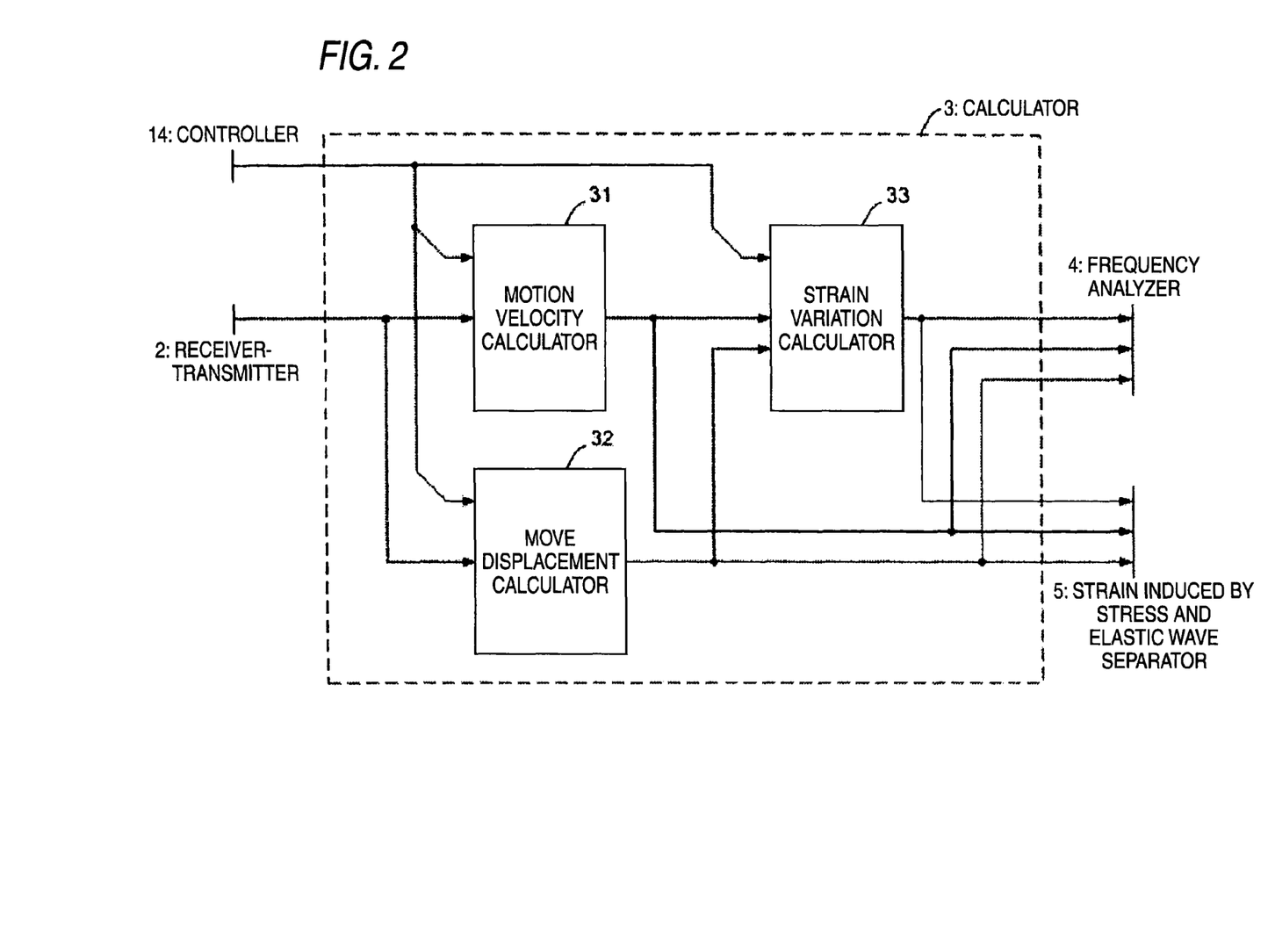
FIG. 2 is a block diagram to show the configuration of a calculator of the ultrasonic diagnostic apparatus of the embodiment of the invention.

FIG. 2 is a block diagram of the calculator 3. The calculator 3 is connected to the frequency analyzer 4 and the strain induced by stress and elastic wave separator 5, and includes either of a motion velocity calculator 31 and a move displacement calculator 32 and a strain variation calculator 33.

The motion velocity calculator 31 uses the ultrasonic echo obtained from within the body tissue through the receiver-transmitter 2 to find the motion velocity of the point of interest or the region of interest set in the body tissue. To detect the motion velocity of the point of interest or the region of interest set in the body tissue, any technique such as an FFT Doppler method or an autocorrelation method generally used may be used or the motion velocity may be found by differentiating the move displacement obtained in the move displacement calculator 32. Since at least two interest points or two interest regions are set, a spatial distribution of the motion velocities can be found. It is also preferred to detect the motion velocities in the proximities of the interest points or the interest regions at the same time and find a mean value of the motion velocities.

The move displacement calculator 32 uses the ultrasonic echo obtained from within the body tissue through the receiver-transmitter 2 to find the move displacement of the point of interest or the region of interest set in the body tissue. To detect the move displacement of the point of interest or the region of interest in the move displacement calculator 32, any technique such as an FFT Doppler method or an autocorrelation method generally used may be used or the move displacement may be found by integrating the motion velocities obtained in the motion velocity calculator 31. Since at least two interest points or two interest regions are set, a spatial distribution of the move displacements can be found. It is also preferred to detect the move displacements in the proximities of the interest points or the interest regions at the same time and find a mean value of the move displacements.

The strain variation calculator 33 finds the strain variation by integrating the differences between the motion velocities of at least two or more interest points or two or more interest regions set on the ultrasonic beam 301, obtained from the motion velocity calculator 31 or using the move displacements of at least two or more interest points or two or more interest regions set on the ultrasonic beam 301, obtained from the move displacement calculator 32. To calculate the strain variation in the strain variation calculator 33, it is also preferred to detect the strain variations in the proximities of the interest points or the interest regions at the same time and find a mean value of the strain variations. A spatial distribution of the strain variations may be found.

The frequency analyzer 4 conducts frequency analysis of the motion velocity of the body tissue and the move displacement found in the calculator 3. The frequency analyzer 4 includes a frequency analysis calculation function of finding the frequency spectrum of biosignals of the motion velocity of the body tissue, the move displacement, etc.

The operation of the frequency analyzer 4 will be discussed below with FIG. 4:

The frequency analyzer 4 calculates the power spectrum difference of motion velocity or move displacement between at least two interest points from the intima to the adventitia of the arterial wall. Based on the nature of the power spectrum difference described above, the frequency component with strain of the arterial wall caused by blood pressure change caused by pulsation of the heart in a frequency band A, the frequency component of vibration caused by flow of blood into the lumen of artery in a frequency band B, and the frequency component of noise in a frequency band C are separated as shown in FIG. 4.

Specifically, the frequency analyzer 4 finds an inflection point of the boundary between the frequency bands A and B of the power vector difference and an inflection point of the boundary between the frequency bands B and C, thereby separating the frequency bands A, B, and C. As shown in FIG. 4, the power spectrum difference of motion velocity or move displacement between two interest points has almost no inclination in the frequency band A, has a negative inclination in the frequency band B, and has a positive inclination in the frequency band C. Therefore, the frequency analyzer 4 can find the inclination of the power vector difference of motion velocity or move displacement between two interest points with respect to the frequency, thereby separating the frequency bands A, B, and C. That is, in the frequency axis in the direction in which the frequency increases from direct current, the inflection point where the inclination changes to negative is determined the boundary between the frequency bands A and B, the direct current to the inflection point is set to the frequency band A, and subsequently the inflection point where the inclination changes from negative to positive is determined the boundary between the frequency bands B and C, the inflection point of the frequency bands A and B to the inflection point of the frequency bands B and C is set to the frequency band B, and the inflection point of the frequency bands B and C to the higher frequency band is determined the frequency band C.

The inflection point can also be found by differentiating the power spectrum difference and detecting the frequency at which a peak occurs. In this case, the boundary between the frequency bands A and B is found by detecting a negative peak and the boundary between the frequency bands B and C is found by detecting a positive peak.

The strain induced by stress and elastic wave separator 5 separates the frequency component with strain of the arterial wall caused by blood pressure change caused by pulsation of the heart, the frequency component of vibration caused by flow of blood into the lumen of artery, and the frequency component of noise based on the determination result of the frequency analyzer 4. The strain induced by stress and elastic wave separator 5 is implemented as a filter and the constant of the filter is automatically set according mainly to the determination result of the frequency analyzer 4.

Figure 5:
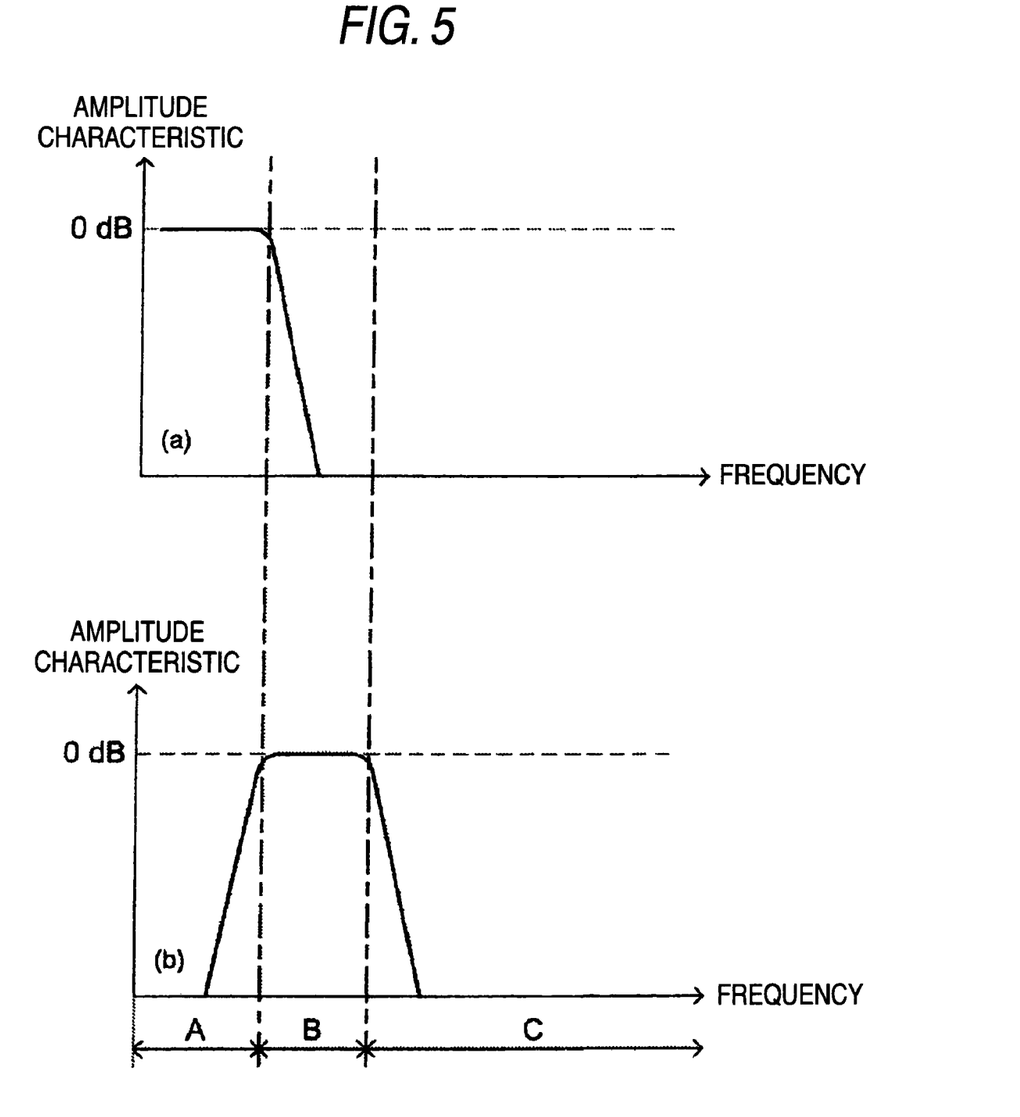
FIG. 5 is a drawing to show an example of the filter characteristic of a filter for implementing a strain induced by stress and elastic wave separator of the ultrasonic diagnostic apparatus of the embodiment of the invention.

FIG. 5 shows an example of the filter characteristic. FIG. 5(*a*) is for separating the frequency component with strain of the arterial wall caused by blood pressure change caused by pulsation of the heart, and FIG. 5(*b*) is for separating the frequency component of vibration caused by flow of blood into the lumen of artery.

The constant of the filter may be able to be set as desired by the user; further, preferably a plurality of filter constants may be preset so that the operation can select any one of the filter constants.

To filter the motion velocity of body tissue and the move displacement in the strain induced by stress and elastic wave separator 5, the filter characteristic is determined using the determination result of the frequency analyzer 4 in the cardiac cycle preceding the target cardiac cycle. Such a technique of filtering the target cardiac cycle data involves short calculation delay time and thus is made possible in a short filtering time in real time and thus is preferred.

Further, the technique of filtering the motion velocity of body tissue and the move displacement in the cardiac cycle using the determination result of the frequency analyzer 4 in the target cardiac cycle in the strain induced by stress and elastic wave separator 5 involves a small data amount required for calculation and thus optimum filtering in real time for making it possible to conduct diagnosis in a short time is made possible and thus the technique is preferred.

Figure 6:
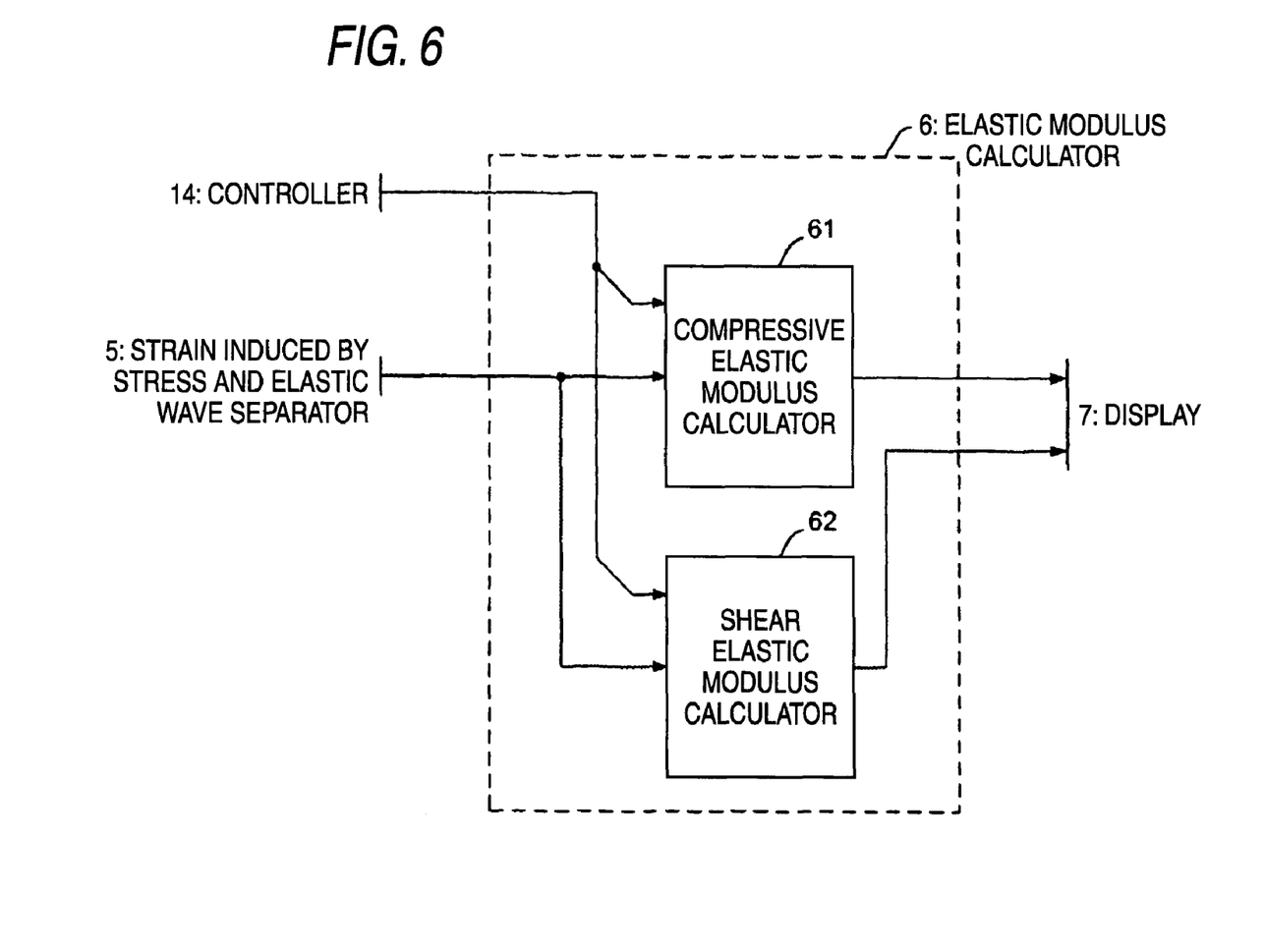
FIG. 6 is a block diagram to show the configuration of an elastic modulus calculator of the ultrasonic diagnostic apparatus of the embodiment of the invention.

FIG. 6 is a block diagram of the elastic modulus calculator 6. The elastic modulus calculator 6 calculates the elastic modulus of the body tissue from the calculation result of the motion of the body tissue obtained in the calculator 3 and includes a compressive elastic modulus calculator 61 and a shear elastic modulus calculator 62.

The compressive elastic modulus calculator 61 divides the strain variation of at least two or more interest points or two or more interest regions set in the body tissue by the stress variation at the identical time using the frequency component with strain of the arterial wall caused by pulsation of the heart to find a compressive elastic modulus. The general compressive elastic modulus of body tissue is calculated from the maximum strain variation and the maximum stress variation; for the arterial wall, the compressive elastic modulus is calculated from the strain variation in one cardiac period and the pulse pressure value (maximal blood pressure—minimal blood pressure). The strain variation is found in the strain variation calculator 33 and is provided by removing the frequency component of vibration caused by flow of blood into the lumen of artery and the noise component in the strain induced by stress and elastic wave separator 5. The stress variation is detected in the stress detector 106 and is provided by removing the frequency component of vibration caused by flow of blood into the lumen of artery and the noise component in the strain induced by stress and elastic wave separator 5.

The shear elastic modulus calculator 62 finds a transfer function H(k) between move displacement of intima of arterial wall 401a and move displacement of adventitia of arterial wall 401b using the frequency component of a shear elastic wave that small oscillation caused by flow of blood into the lumen of artery propagates from the intima to the adventitia of the arterial wall, and finds a shear elastic modulus $\mu_1$ and/or a shear viscosity $\mu_2$ from the gain characteristic and the phase characteristic of the transfer function H(k). The transfer function H(k) can be calculated according to (expression 9) using a cross spectrum method.

[Number 7]

$$H(k) = \frac{E_i[X_i^*(k)Y_i(k)]}{E_i[|X_i(k)|^2]}$$ (Expression 9)

Where Xi(k) is a frequency spectrum of input signal, namely, a frequency spectrum of the move displacement of intima of arterial wall 401a and Yi(k) is a frequency spectrum of output signal, namely, a frequency spectrum of the move displacement of adventitia of arterial wall 401b. i denotes the ith cardiac period of M cardiac periods and takes a value 1 . . . i . . . M. k means a discrete frequency, * means a complex conjugate, and E means average operation of the cardiac periods.

The transfer function H(k) is a complex number and attenuation (gain) characteristic α and phase characteristic β are found by assigning exp(jω) to k of the transfer function H(k), finding real part component Re{H(jω)} and imaginary part component Im{H(jω)}, and calculating absolute value |H(jω)| and angle ∠H(jω) using (expression 10) and (expression 11).

[Number 8]

$$\alpha = |H(j\omega)| = \sqrt{\text{Re}\{H(j\omega)\}^2 + \text{Im}\{H(j\omega)\}^2}$$ (Expression 10)

$$\beta = \angle H(j\omega) = \arctan\frac{\text{Im}\{H(j\omega)\}}{\text{Re}\{H(j\omega)\}}$$ (Expression 11)

Further, the shear elastic modulus calculator 62 finds the shear elastic modulus $\mu_1$ and/or the shear viscosity $\mu_2$ using (expression 2) described above from the attenuation α and the phase β found from the gain characteristic of the transfer function H(k) found using (expression 9) to (expression 11).

As described above, the shear elastic modulus calculator 62 finds the shear elastic modulus $\mu_1$ and/or the shear viscosity $\mu_2$ from the attenuation α and the phase β found from the transfer function H(k), so that it is made possible to keep track of the viscoelasticity of the body tissue simply by measuring vibration of any desired frequency (single frequency).

The display 7 displays information based on the elastic modulus calculation result the elastic modulus calculator 6, namely, the elastic characteristic of the body tissue obtained in the elastic modulus calculator 6. Preferably, the elastic modulus is displayed corresponding to the biological body position indicated by a B mode tomographic image of a display function of a general ultrasonic diagnostic apparatus. At the time, the elastic modulus may be displayed in a numeric value or may be displayed with display color changed in response to the value. The information indicating the elastic modulus may be superposed on a B mode tomographic image for display or may be displayed as another image. If an ultrasonic beam is scanned and the elastic moduli of a plurality of interest points or interest regions are found, it is also preferable to convert the elastic moduli into colors and superpose the colors on a B mode tomographic image for display. As the displayed elastic modulus, the compressive elastic modulus found from strain of the arterial wall caused by pulsation of the heart and either of the shear elastic modulus found according to the propagation characteristic of the shear elastic wave propagating from the intima to the adventitia of the arterial wall and the shear viscosity may be displayed in an overlap manner or only either of the shear elastic modulus and the shear viscosity may be displayed.

In the description given above, to find the shear elastic modulus $\mu_1$ and/or the shear viscosity $\mu_2$, the shear elastic modulus calculator 62 uses the attenuation α and the phase β found from the transfer function H(k), but can also use only the attenuation α to find the shear elastic modulus $\mu_1$ and/or the shear viscosity $\mu_2$. This calculation uses the fact that approximation can be made to a linear function as shown in (expression 3) to (expression 6) in the frequency band where the square value of the attenuation α of the shear elastic wave becomes $\omega\mu_2 \gg \mu_1$.

The shear elastic modulus calculator 62 estimates a linear line based on the frequency of the square value of the attenuation α of the shear elastic wave from the power vector difference of the vibration velocity of tissue between the move displacement of intima of arterial wall 401a and the move displacement of adventitia of arterial wall 401b, and finds the shear elastic modulus $\mu_1$ and/or the shear viscosity $\mu_2$ using (expression 5) and (expression 6) described above. To thus estimate the shear elastic modulus $\mu_1$ and the shear viscosity $\mu_2$ of body tissue using only the attenuation α, the calculation amount can be lessened.

The attenuation α of the shear elastic wave may be found from the square value of the absolute value of the transfer function H(k) shown in (expression 10) as in the first embodiment. To find the linear line from the power vector difference or the transfer function H(k), preferably a least squares method is used.

Figure 8:
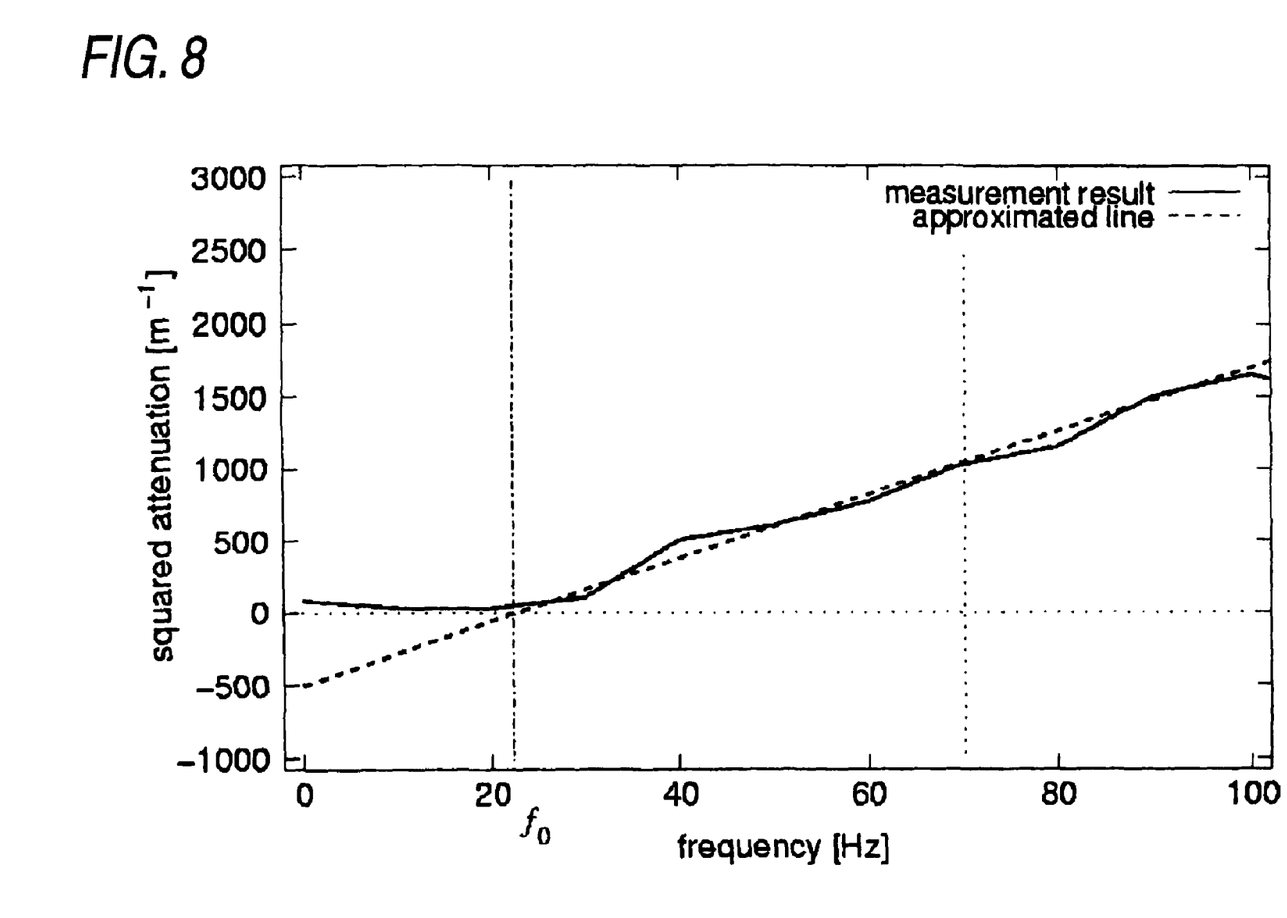
FIG. 8 is a drawing to show the frequency characteristic of the square value of the attenuation of vibration propagation from the intima to the adventitia of the rear wall of the carotid wall of an able-bodied male being 28 years old and the frequency characteristic approximated by a linear function.

FIG. 8 shows the frequency characteristic of the square value of the attenuation of vibration propagation (mainly, shear elastic wave propagation is the main factor) from the intima to the adventitia of the rear wall of the carotid wall of an able-bodied male being 28 years old and the frequency characteristic approximated by a linear function. From FIG. 8, it is seen that the square value of the attenuation of vibration propagation increases linearly with an increase in the frequency in a frequency band of about 30 to 100 Hz.

An approximated line is found from the result shown in FIG. 8 and the shear elastic modulus $\mu_1$ and the shear viscosity $\mu_2$ are found based on (expression 4). The results are $\mu_1$=22 kPa and $\mu_2$=156 Pa·s. It is seen that angular frequency $\omega_0$ of the inflection point transiting from (expression 7) to (expression 4) exists in the vicinity of 23 Hz from the ratio between the shear elastic modulus $\mu_1$ and the shear viscosity $\mu_2$.

In the ultrasonic diagnostic apparatus described above, the compressive elastic modulus found from strain of the arterial wall caused by pulsation of the heart and stress change and either of the shear elastic modulus based on the propagation characteristic of the elastic wave and the shear viscosity are calculated, but only either of the shear elastic modulus and the shear viscosity may be calculated without calculating the compressive elastic modulus. In this case, the stress detector 106 shown in FIG. 1, the strain variation calculator 33 shown in FIG. 2, and the compressive elastic modulus calculator shown in FIG. 6 are not required.

While the invention has been described in detail with reference to the specific embodiments, it will be obvious to those skilled in the art that various changes and modifications can be made without departing from the spirit and the scope of the invention.

This application is based on Japanese Patent Application (No. 2005-345772) filed on Nov. 30, 2005, which is incorporated herein by reference.

INDUSTRIAL APPLICABILITY

The invention is used preferably for an ultrasonic diagnostic apparatus for measuring the shape characteristic or the property characteristic of body tissue. Particularly, the invention is used preferably for an ultrasonic diagnostic apparatus that can make a diagnosis of the body tissue by measuring the elastic modulus of the body tissue of an arterial wall, etc.

The invention claimed is:

1. An ultrasonic diagnostic apparatus for measuring a shape characteristic or a property characteristic of body tissue, comprising:
    a velocity calculator which calculates a motion velocity of the body tissue and a move displacement calculator which calculates a move displacement of the body tissue;
    a strain variation calculator which calculates a strain variation of the body tissue based on the motion velocity or the move displacement;
    a stress variation detector which detects a stress variation applied to the body tissue;
    a frequency analyzer which conducts frequency analysis on the motion velocity and the move displacement and determines a frequency of a power spectrum difference of the motion velocity and the move displacement between a plurality of different points of interest on the body tissue;
    a strain induced by stress and elastic wave separator which separates, approximately at the frequency as determined by the frequency analyzer, a strain induced by stress component based on motion of the body tissue caused by stress change of the body tissue motion and an elastic wave component based on an elastic wave propagation characteristic propagating in the body tissue, from the motion velocity, the move displacement, the strain variation, and the stress variation; and
    an elastic modulus calculator which calculates a compressive elastic modulus based on motion of the body tissue caused by stress change based on the strain variation and the stress variation, and also calculates at least one of shear elastic modulus and shear viscosity modulus based on the elastic wave propagation characteristic.

2. The ultrasonic diagnostic apparatus as claimed in claim 1, wherein:
    the velocity calculator, the move displacement calculator, and the strain variation calculator have functions of finding spatial distributions of the motion velocity, the move displacement, and the strain variation on a plurality of interest points or interest regions set in the body tissue.

3. The ultrasonic diagnostic apparatus as claimed in claim 1, wherein:
    the velocity calculator, the move displacement calculator, and the strain variation calculator have functions of finding spatial average values of the motion velocities, the move displacements, and the strain variations.

4. The ultrasonic diagnostic apparatus as claimed in claim 1, wherein:
    the frequency analyzer has a function of calculating frequency characteristic of a transfer function on the motion velocity and the move displacement between at least two or more interest points in the body tissue.

5. The ultrasonic diagnostic apparatus as claimed claim 1, wherein:
    the strain induced by stress and elastic wave separator is implemented as a band-pass filter and/or a band limiting filter.

6. The ultrasonic diagnostic apparatus as claimed in claim 1, further comprising:
    a display for displaying information based on the calculation result of the elastic modulus calculator.

7. The ultrasonic diagnostic apparatus as claimed in claim 1, wherein:
    the frequency analyzer has a function of calculating a power spectrum difference or the square value of the attenuation on the motion velocity and the move displacement between at least two or more interest points in the body tissue, and further calculating an inclination relative to the power spectrum difference or the frequency of the square value of the attenuation.

8. The ultrasonic diagnostic apparatus as claimed in claim 7, wherein: the strain induced by stress and elastic wave separator separates the strain induced by stress components and the elastic wave components of the motion velocity, the move displacement, the strain variation, and the stress variation based on the inclination relative to the power spectrum difference or the frequency of the square value of the attenuation and further removes a noise component.

9. An ultrasonic diagnostic apparatus for measuring a shape characteristic or a property characteristic of body tissue, comprising:
    a velocity calculator which calculates a motion velocity of the body tissue and a move displacement calculator which calculates a move displacement of the body tissue;

a frequency analyzer which conducts frequency analysis on the motion velocity and the move displacement and determines a frequency of a power spectrum difference of the motion velocity and the move displacement between a plurality of different points of interest on the body tissue;

a strain induced by stress and elastic wave separator which separates, approximately at the frequency determined by the frequency analyzer, a strain induced by stress component based on motion of the body tissue caused by stress change of the body tissue motion and an elastic wave component based on an elastic wave propagation characteristic propagating in the body tissue, from the motion velocity and the move displacement; and an elastic modulus calculator which calculates at least one of shear elastic modulus and shear viscosity modulus based on the elastic wave propagation characteristic.

10. The ultrasonic diagnostic apparatus as claimed in claim 9, further comprising:

a display for displaying information based on the calculation result of the elastic modulus calculator.

* * * * *

UNITED STATES PATENT AND TRADEMARK OFFICE
CERTIFICATE OF CORRECTION

PATENT NO. : 8,052,602 B2  
APPLICATION NO. : 12/095381  
DATED : November 8, 2011  
INVENTOR(S) : Kazuhiro Sunagawa and Hiroshi Kanai Page 1 of 1

It is certified that error appears in the above-identified patent and that said Letters Patent is hereby corrected as shown below:

On the Title Page:

Item (73) Assignee should be listed as:

Panasonic Corporation, Osaka (JP) and Tohoku University, Miyagi (JP)

Signed and Sealed this  
Ninth Day of October, 2012

David J. Kappos  
*Director of the United States Patent and Trademark Office*